United States Patent [19]
Vander Heyden et al.

[11] Patent Number: 5,882,115
[45] Date of Patent: *Mar. 16, 1999

[54] MEASURING HEATING VALUE OF A GAS USING FLAMELESS COMBUSTION

[75] Inventors: William H. Vander Heyden, Mequon, Wis.; Ronald Arthur Berg, Tulsa, Okla.

[73] Assignee: Badger Meter, Inc., Milwaukee, Wis.

[ * ] Notice: The term of this patent shall not extend beyond the expiration date of Pat. No. 5,820,260.

[21] Appl. No.: 993,236

[22] Filed: Dec. 18, 1997

Related U.S. Application Data

[62] Division of Ser. No. 682,828, Feb. 12, 1996, Pat. No. 5,816,705.

[51] Int. Cl.$^6$ .................................................. G01N 25/22
[52] U.S. Cl. .............................................. 374/37; 374/36
[58] Field of Search ........................................ 374/36, 37

[56] References Cited

U.S. PATENT DOCUMENTS

| | | |
|---|---|---|
| 3,926,562 | 12/1975 | Williams et al. . |
| 4,285,245 | 8/1981 | Kennedy . |
| 4,329,873 | 5/1982 | Maeda et al. . |
| 4,351,614 | 9/1982 | Garnier ..................................... 374/37 |
| 4,386,858 | 6/1983 | Kude et al. ................................ 374/37 |
| 4,533,258 | 8/1985 | Milovidov ................................. 374/37 |
| 5,012,432 | 4/1991 | Stetter et al. ............................. 374/37 |
| 5,165,884 | 11/1992 | Martin et al. . |
| 5,201,581 | 4/1993 | Vander Heyden et al. .............. 374/37 |
| 5,226,728 | 7/1993 | Vander Heyden ........................ 374/37 |
| 5,320,518 | 6/1994 | Stilger et al. . |
| 5,482,679 | 1/1996 | Dijkstra et al. ........................... 374/37 |

FOREIGN PATENT DOCUMENTS

| | | |
|---|---|---|
| 0 304 266 | 2/1989 | European Pat. Off. . |
| 0326494 | 8/1989 | European Pat. Off. ................. 374/37 |
| 85 02908 | 7/1985 | WIPO . |
| 90 10222 A | 9/1990 | WIPO . |

OTHER PUBLICATIONS

English abstract of JP 58115358, published Sep. 7, 1983 (Patent Abstracts of Japan).

*Primary Examiner*—Randy W. Gibson
*Attorney, Agent, or Firm*—Quarles & Brady

[57] ABSTRACT

The heating value of a sample gas is calculated by a microcontroller (12) from the heating value of a reference gas, and from flow ratios and power levels determined as the gas is combusted by a flameless combustion process. The combustible gas is mixed with a combustion supporting gas, such as air, and flowed to a body of material (26, 52) which is heated to a temperature sufficient for oxidation of the gas mixture. The size of spaces in a first embodiment of a heater device (9, 11, 25, 26) and in a second embodiment of a heater device (50) are limited to prevent formation of an open flame. In a preferred "lean mixture" embodiment, the gas-air mixture of the reference gas, and the gas-air mixture of the sample gas, respectively, are each adjusted until a selected power level of combustion at a temperature lower than the point of stoichiometric combustion is reached. In a second, "rich mixture" embodiment, the gas-air mixture of the reference gas, and the gas-air mixture of the sample gas, respectively, are each adjusted from a "rich mixture" to reach a point of stoichiometric combustion. Based on flow rates and the selected power ratio, the heating value of the sample gas is calculated by the microcontroller (12) and output to a visual display or other output device.

21 Claims, 4 Drawing Sheets

MEASURING HEATING VALUE OF A GAS USING FLAMELESS COMBUSTION

CROSS-REFERENCE TO RELATED APPLICATION

This is a division of application Ser. No. 08/682,828 filed Jul. 12, 1996, now U.S. Pat. No. 5,16,705.

TECHNICAL FIELD

The field of the invention is methods and apparatus for determining the heating value of gases.

DESCRIPTION OF THE BACKGROUND ART

The measurement of the heating value of natural gas is important in controlling combustion and is a necessary measurement in the distribution and sale of natural gas. There are four useful methods for measuring heating value.

The first method for measuring heating value is calorimetric measurement in which a volume of the gas is combusted. An amount of heat is liberated by the complete combustion and is carefully accumulated and measured. The amount of heat liberated is manifested by a change in temperature. This method is the original method employed and usually requires extreme control of flows and temperatures. The apparatus usually requires extensive maintenance.

The second method for measuring heating value is constituent analysis. Using a gas chromatograph, the fraction of each chemical constituent in the gas is determined. Then heating value is determined by summing the heating values for the individual constituents according to their fractional presence. The problem with constituent analysis is the reliability of the apparatus and its linearity. Gas chromatographs require constant maintenance and have a limited range for heating value measurement unless calibrated with a reference gas that is very similar to the sample gas.

The third method is stoichiometry, in which combustion is substantially completed with a perfect amount of oxygen. In this case, natural gases are combusted with air and the fuel-to-air ratio is adjusted until combustion results in either a maximum flame temperature or the stoichiometric point of perfect combustion, i.e., the knife edge when there is no remaining oxygen.

Clingman, U.S. Pat. No. 3,777,562, is an example of the third method. In Clingman, heating value is measured by combustion of a gas with amounts of air that are adjusted to obtain the maximum flame temperature. This is further disclosed in Clingman, U.S. Pat. Nos. 4,062,236, 4,125,018 and 4,125,123. In each of these patents, the combustion of the air-gas mixture is accomplished with a combustion flame on a burner top and with a temperature sensing device such as a thermocouple. Certain environments cannot be served by equipment that presents an open flame.

The fourth method utilizes catalytic combustion. Gas is passed over a heated catalyst and oxidized. The amount of heat liberated can be measured either by temperature changes related to the catalytic reaction, by changes in power supplied to heat the catalyst or by measuring the temperature of the catalytic material. Catalytic combustion or catalytic oxidation is a known phenomenon with hydrocarbons. A mixture of hydrocarbon gas and air in the presence of platinum and/or palladium material will produce an oxidation reaction. The reaction occurs at temperatures below the auto-ignition temperature associated with a hydrocarbon. For example, methane when mixed with air will ignite at a temperature of about 730° C. and reach an open flame at a temperature exceeding 1600° C. Catalytic oxidation can take place at catalyst temperatures as low as 400° C. although efficient catalytic activity is achieved at temperatures near 500°–600° C.

One problem with catalytic oxidation is the potential for poisoning the catalyst. Certain chemicals such as sulfur or lead and numerous others, can combine with and disable a catalyst and therefore eliminate its usefulness in heating value measurement. In many processes, such as land fill gas recovery, the gases contain "poisons" in sufficient quantity to have a high probability of disabling the measurement process.

SUMMARY OF THE INVENTION

The present invention provides methods and apparatus for measuring the heating value of a gas utilizing non-catalytic flameless combustion and variable molar flow rates for sample gas mixtures fed to the combustion apparatus. The combustion process operates at a temperature sufficient for combusting temperature of a gas mixture while quenching any an open flame, thereby making the process suitable for operation in special environments.

The present invention utilizes a body of inert material for receiving and combusting mixtures of gases and a carrier gas, such as air. Under normal conditions, the gas would be oxidized or combusted and a flame would form. In the present invention, inert material is formed with only small voids, so that an open flame is prevented by the quenching of rapid heat transfer.

In most heating value measurements, extreme stability of gas and air volumes is required to achieve accuracy. Many of the previously described methods use constant flow rates or constant gas volumes. The present invention eliminates the need for such constant values.

In addition, the oxidation or combustion of the present invention can be performed with mixture concentrations over a wide range that extends beyond the stoichiometric mixture of the gas. This process cannot be "poisoned" in the catalytic sense, because no catalyst is involved in the combustion.

The gas combustion power or the combustion temperature, is measured as the gas mixture flows in the combustion device. The associated molar flow rate of the gas is also measured. A reference gas and the sample gas are measured alternately and repeatedly. The only requirement is that the molar flow rate of the sample and reference gas be compared at an appropriate combustion power or at a maximum combustion temperature for the combustion device.

In one embodiment, air flow is established well in excess of the air required to combust the gas, a lean gas condition. The combustion gas is mixed with air, and the mixture is flowed over or through a heated body of solid material and the mixture is oxidized. The combustion power and the gas molar f low rate vary with time. At a selected combustion power, the molar flow rate of the gas is measured by appropriate sensors, and along with the known heating value of a reference combustion gas are used to calculate the heat value of a sample combustion gas.

In a second embodiment, air flow is established below the air flow required to combust the gas at stoichiometric conditions, to provide a rich gas mixture. The combustion gas is again mixed with the air, and the gas-air mixture is flowed into contact with a heated body of solid material where the mixture is oxidized. The combustion power is measured continuously. The molar f low rate of the gas is determined when the electrical combustion of the electrical heater power reaches a minimum value corresponding to the maximum value of gas combustion. At this maximum gas combustion power, the molar flow rate of the gas is measured by appropriate sensors.

In both a "lean mixture" embodiment and a "rich mixture", embodiment, a reference gas cycle is followed by one or more sample gas cycles.

For the embodiment using the lean gas mixture, the heating value of the sample gas is calculated based on the known heating value of the reference gas, the power levels of combustion selected for the reference gas and the sample gas, the flow rates of the reference gas and the sample gas at the selected power levels, and in some instances a ratio of the power levels for the reference gas and the sample gas.

For the embodiment using the rich gas mixture, the heating value of the sample gas is calculated based on the known heating value of the reference gas, the power level of combustion corresponding to stoichiometric combustion, and the flow rates of the reference gas and the sample gas at the power level for stoichiometric combustion.

In either embodiment, the fuel-to-air mixture may be varied by allowing pressure in a volume chamber to decay, to produce a decreasing flow of fuel that progressively leans out the fuel-to-air mixture. Molar flow rates are measured for a reference gas and a sample gas during respective combustion cycles occurring within the heated body of solid material. The heating value for the reference gas is typically a value stored in memory. The fuel-air mixture may also be varied by direct control of the flow rates of the air and gases using conventional pressure controllers, for example.

Various objects and advantages will be apparent to those of ordinary skill in the art from the description of the preferred embodiment which follows. In the description, reference is made to the accompanying drawings, which form a part hereof, and which illustrate examples of the invention. Such examples, however, are not exhaustive of the various embodiments of the invention, and, therefore, reference is made to the claims which follow the description for determining the scope of the invention.

BRIEF DESCRIPTION OF THE DRAWINGS

FIG. 3a is a schematic diagram of a combustion device used in the apparatus of FIG. 1;

FIG. 3b is a graph of temperature versus longitudinal displacement within the combustion device of FIG. 3a;

FIG. 3c is a schematic diagram of a second embodiment of a combustion device used in the apparatus of FIG. 1;

DETAILED DESCRIPTION OF THE PREFERRED EMBODIMENTS

Figure 1:
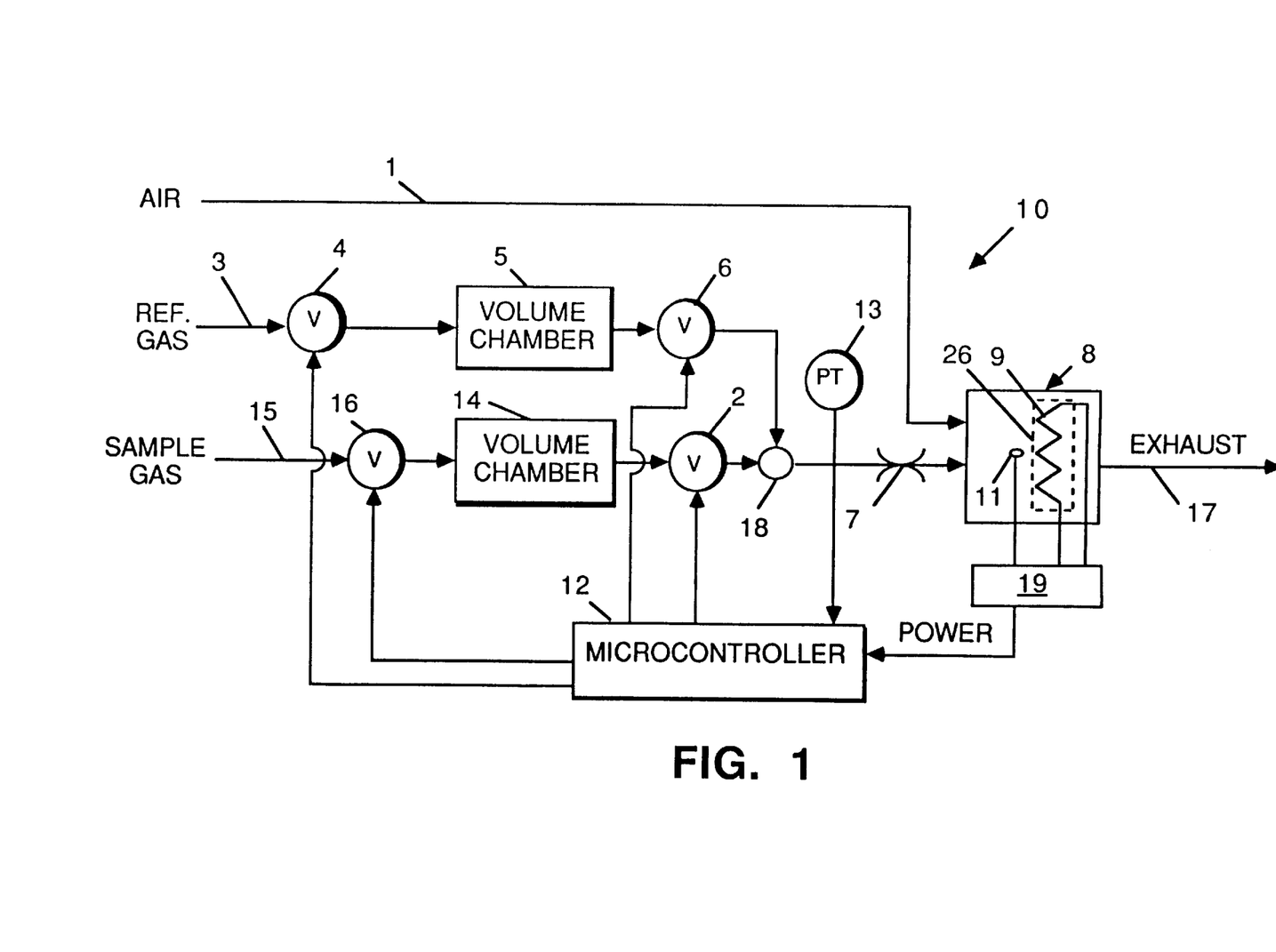
FIG. 1 is a block diagram of an apparatus for practicing the method of the present invention.

Referring to FIG. 1, an apparatus 10 for practicing the method of the present invention receives air from an external supply through supply line 1. The air is used as a carrier gas and to flush other gases from combustion apparatus 8. A reference gas is received from an external supply through supply line 3. A sample gas, for which the heating value is to be determined, is received from an external supply through supply line 15.

Figures 3A, 3B, 3C:
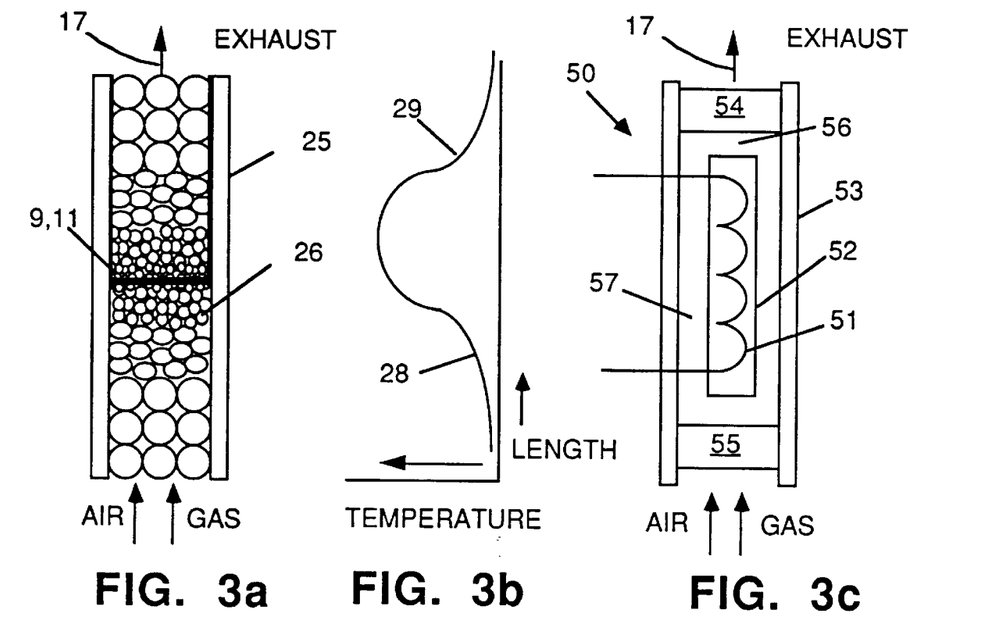

The reference gas and the sample gas are to be mixed with varying amounts of air as a combustion supporting gas and combusted in a combustion apparatus 8 that includes a heating element 9, a temperature sensor 11 and a porous body of inert solids (26 in FIG. 3) which are heated by heating element 9.

The porous body of inert solids 26 is composed of solids having high temperature and high heat capacity and is usually formed of ceramic materials. The heating element 9 is located at or in the central section of the porous body 9 to provide an initial starting temperature for the reaction. The inert solids 26 are typically heated to a temperature of 800° C. or more.

Heating element 9 is energized by electricity from a power supply circuit 19 (FIG. 1). Temperature sensor 11 is embedded in the porous material to sense the temperature at the reaction surface of the porous material. Temperature sensor 11 generates a signal as an input to power source 19. This signal is recognized by the power source 19 as representative of reaction temperature.

The products of combustion are exhausted from the combustion apparatus 8 in an exhaust stream 17. Additional steps may be taken to process the exhaust stream.

Microcontroller 12 is a suitable microelectronic CPU (central processing unit) with A-to-D and D-to-A interface circuitry. Microcontroller 12 operates by executing program instructions, some of which are represented by blocks in the flow chart in FIG. 5, the instructions being stored in a memory also represented generally by reference 12.

The apparatus 10 includes elements for producing variable flow rates of air and combustible gas to vary the mixtures for the reference gas and the sample gas, respectively. The apparatus 10 more particularly includes outlet control valves 2 and 6 for controlling the flow of sample gas or reference gas, respectively, to restrictor 7. The outlet flow rate is determined by the initial charging pressure in volume chamber 5, 14 and the flow properties of flow restrictor 7. It is preferred that the flow rates of the air-gas mixtures be continuously variable over some range. However, the invention could also be employed with constant flow rates in other embodiments. And, although the preferred embodiments described more fully herein adjust the mixtures by adjusting the flow rates of the combustible gases, it is also known that such mixtures can be adjusted by adjusting the flow rate of the air.

The supply line 3 for the reference gas is connected through inlet flow control valve 4 to volume chamber 5. Flow control valve 6 is closed during filling of volume chamber 5 to close the outlet. When gas pressure in volume chamber 5 reaches a predetermined but non-critical level, usually set by the pressure of the external supply line 3, then inlet control valve 4 is closed.

Following closure of valve 4, outlet control valve 6 is opened allowing flow of gas from volume chamber 5 through flow restrictor 7, where it is then mixed with air flow from supply line 1 and passed through a porous body of inert solids 26.

One way to measure the temperature of combustion is to monitor the electrical power that is provided to the heater device 8 from power supply circuit 19 to maintain a constant temperature at sensor 11. Changes in this electrical power supplied to heater 9 are a measure of the change in combustion power or combustion temperature of the combustion process in combustion apparatus 8.

As gas flows out of volume chamber 5, the pressure in volume chamber 5 is reduced. Microcontroller 12 monitors the changes in pressure in volume chamber 5 using a pressure transducer 13. At a preselected level of combustion, as sensed through power supply circuit 19, a molar flow rate or a change in molar content in chamber 5 is measured or calculated, and then stored by microcomputer 12. When the gas pressure in volume chamber 5 reaches a predetermined, but not critical, low level, control valve 6 is closed, thereby stopping the flow of the reference gas to the combustion apparatus 8.

While reference gas has been flowing to combustion apparatus 8, control valve 16 has been open to fill the volume chamber 14 with sample gas from supply line 15. Flow into volume chamber 14 increases pressure in volume chamber 14 until a predetermined but non-critical pressure is reached, usually determined by the pressure in supply line 15, and then inlet control valve 16 is closed. When sample gas is to be flowed to combustion apparatus 8, microcontroller 12 opens control valve 2 to establish flow of sample gas through restrictor 7 to combustion apparatus 8, where the mixture of sample gas and air is combusted.

Power supply circuit 19 continuously adjusts power to heater 9 to maintain a constant temperature as sensed by sensor 11. As the gas flow rate reduces, power changes to the heater 9 are inversely proportional to the heat energy of combustion in apparatus 8. Depending on the embodiment, the molar flow rate from volume chamber 14 is calculated and stored by microcomputer 12 for a) a predetermined combustion power level or b) a predetermined change in combustion power level or c) at the maximum temperature condition.

It should be noted that measurement of molar flow rate using the rate of change of pressure in volume chamber 5, 14, is of the type disclosed in Kennedy, U.S. Pat. No. 4,285,245 for sensing molar flow rate in response to pressure changes due to flow of gas out of a chamber. This eliminates the molecular weight of the gas from consideration in the gas measurements. Such a flow meter is incorporated in a product commercially offered by the assignee under the trade designation "TRU-THERM".

The use of two volume chambers, 5 and 14, is not required but is a preferred embodiment. Using one chamber would slow the measurement process because a single chamber utilizing two gases would require several cycles to exhaust a residue of a combustible gas remaining in the chamber from a previous cycle. If speed of response is not a primary goal of design, the measurement can be modified to use reference gas only infrequently and a single volume chamber can be used.

Figure 2:
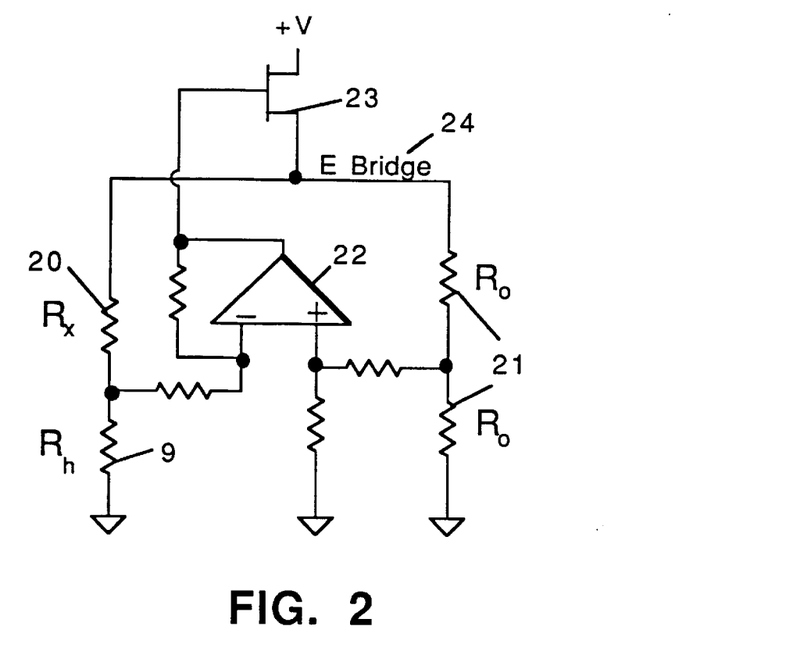
FIG. 2 is a detail schematic diagram of an electrical circuit in the catalytic apparatus of FIG. 1.

FIG. 2 illustrates the power supply circuit 19, temperature sensor 11 and heater 9 described earlier in relation to FIG. 1. The circuit 19 is a bridge that maintains a constant resistance by heating and cooling by electrical means.

In the preferred embodiment, resistance 9 in FIG. 2 is provided by a platinum coiled-wire resistor. Platinum is selected due to its stable temperature coefficient over a wide temperature range. The resistance is $R_h=R_{h0}(1+\alpha\Delta T)$. The value of resistor 20 and resistor 9 are selected to provide the desired temperature of operation at the power levels selected for the operation of the porous body of solids 26 (FIG. 3a). The coiled-wire resistor provides both the resistance heating element 9 and the temperature sensor 11 for the porous material 26. Resistors 21 are a pair of resistors that divide the voltage 24 applied to the bridge. In FIG. 2, the resistors 21 are shown with equal values, $R_o$, which is not a strict requirement.

In FIG. 2, operational amplifier 22 senses the difference between the center tap voltages on each section of the bridge and amplifies that difference. The result is applied to power FET 23 and changes the voltage 24 on the bridge until the center tap voltages of the two sections become equal.

Therefore, the electrical power level into the heater-sensor 9, 11 is that required to hold the resistance and temperature of heater-sensor 9, 11 constant. If gas combustion takes place, the heat of combustion will raise the temperature of material 26 and the applied electrical power will be proportionately reduced to maintain a constant temperature for the heater-sensor 9, 11.

FIG. 3a depicts the general construction of a heater device by forming a column of porous inert material 26. A tube 25 holds the porous material, in this example, beads 26 of different sizes, and forms a column. Ceramic beads or foam can be used as the porous solids 26, and if foam is used, the body may be a unitary body. Beads can be graduated in size as well as have a changing surface character to control emission of radiation components, which affect the heat transfer rate from the combustion products. The heater-sensor 9, 11 is located in the central section of the porous material 26 and through resistance heating raises the temperature of the material 26 to a level greater than the auto-ignition temperature of the gas-air mixture.

The small voids in the porous body of solid material 26 are selected and characterized by having a linear dimension on the order of the quenching dimension of the gas flame. With methane, for example, the quenching dimension is about 2.5 millimeters (0.060"). The methane does not burn with an open flame when the voids in the body of solid materials 26 are smaller than 2.5 mm. Heat is transferred through the solid material 26 at a sufficient rate to prevent the large increases in temperature that would accompany an open flame.

Combustion produces combustion products such as $CO_2$ and $H_2O$ vapor. A flame is a visual indication that the combustion products have insufficient heat capacity to carry away the heat of combustion by convection and conduction alone. The temperature of the combustion products must then rise until the radiation level is high enough to radiate the excess heat. The rate of conduction and convection increases in linear relation to temperature. Radiation responds in proportion to the fourth power of temperature, and provides an additional and stabilizing factor to the heat transfer rate. The temperature of the burned gases increases until the heat of combustion equals the heat losses. For natural gases, the gas temperature reaches radiation frequencies in the visible spectrum and the flame is visible.

In the present invention, gas flow rates through the combustion apparatus 8 are also limited by design to limit the total available heat of the combustion reaction. If the energy available from combustion is too great, electrical power cannot be reduced enough to control the combustion. Therefore, limits are placed on the flow rate of the gas-air mixture to limit the heating power available by combustion to less than the electrical power required to heat the solid material 26 above the auto-ignition temperature.

The solids structure surrounding the small voids allows the heat transfer rate between the combustion gas products and the heater to be sufficiently high to prevent large temperature increases and thereby stabilize the combustion temperature. The body of material 26 must have sufficient heat transfer capacity to quench the flame without requiring high radiation temperatures.

The air and the gas are introduced at the base of the column and travel through the body of material 26. Because of heat flow from the central section, the temperature 28 (FIG. 3b) of the inlet section of the combustion material 26 increases and the gas-air mixture heats and mixes as it flows toward the reaction zone at the center.

Beyond the reaction zone, the temperature 29 (FIG. 3b) in the column 25 cools as the gases pass to the exhaust 17. The temperature profile of the porous bed is indicated in the accompanying graph in FIG. 3b.

When the air-gas mixture reaches the reaction zone, and when the temperature is above the auto-ignition point, the gas oxidizes or combusts to release energy as the heat of combustion. The released heat raises the temperature of the reaction zone and raises the resistance of the platinum heater 9. The power supply circuit 19 for the heating element 9 senses this increasing temperature and reduces the electrical power to maintain a constant temperature in the reaction zone. The change in electrical power corresponds to the increased combustion power or porous bed temperature and is the indicator of porous bed activity.

FIG. 3c illustrates an alternative embodiment of a heater device 50. A coil of platinum wire 51 is cast into a body of ceramic material 52. An outer structure for the heater device 50 comprises upstanding wall(s) 53, and the device is cylindrical, but may be rectangular or other shapes in cross section in other embodiments. Filter elements 54, 55 are made of porous metal to allow passage of gas mixtures, while filtering out particulate matter. The filter elements 54, 55 form the upper and lower end walls of the heater device 50. The upstanding wall 53 and filter elements 54, 55 are closely spaced from the heating element 51, 52, so as to provide spaces 56, 57 of suitably small dimension to quench any higher temperature reactions before a flame is formed.

The spaces 56, 57 are selected and characterized by having a linear dimension on the order of the quenching dimension of the gas flame. With methane, for example, the quenching dimension is about 2.5 millimeters (0.060"). The methane does not burn with an open flame when the spaces 56, 57 are smaller than 2.5 mm. Heat is transferred through the solid material 52 at a sufficient rate to prevent the large increases in temperature that would accompany an open flame.

In operation, the coil 51 is supplied by electrical power from power circuit 19 (FIG. 1). As the mixed gas flows through the heater 50, it oxidizes and and produces heat in a normal fashion but the heat transfer rate to the surrounding wall 53 is sufficiently rapid to enable the gases to cool without significantly increasing the combustion product temperatures. This is known as "quenching" the flame. If the heater is operated at a constant temperature above the auto-ignition temperatures for the mixed gases, then as combustion power increases, the electrical power must be decreased to reflect the magnitude of the combustion power liberated by the mixed gases.

In a preferred "lean mixture" embodiment, the gas-air mixture of the reference gas, and the gas-air mixture of the sample gas, respectively, are each variably decreased until a selected power level of combustion at a gas combusting power lower than the point of stoichiometric combustion is reached. In a second, "rich mixture" embodiment, the gas-air mixture of the reference gas, and the gas-air mixture of the sample gas, respectively, are each variably decreased from a "rich mixture" to reach a point of stoichiometric combustion, which corresponds to the highest power of combustion within the body of solids 26, 52.

Figure 4A:
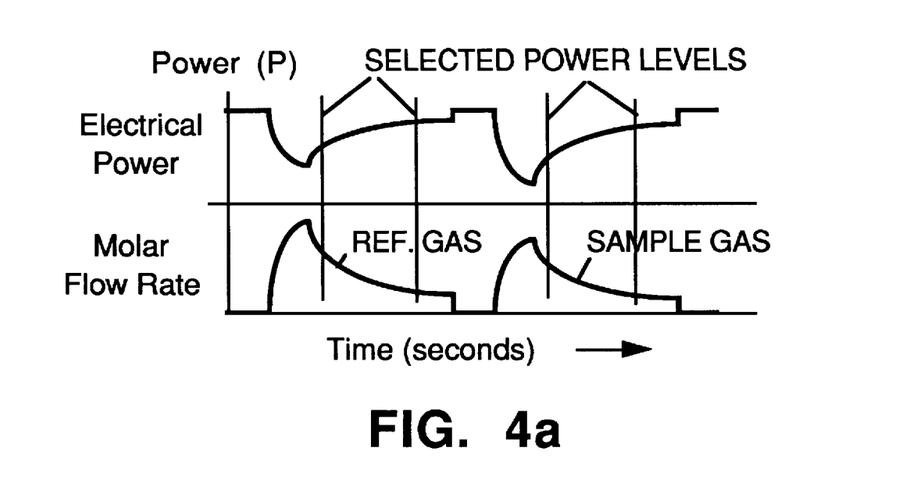
FIG. 4a and 4b are graphs of power and molar flow rate versus time illustrating operation of the apparatus of FIG. 1.

The molar heating value, $H_m$, is defined as the amount of heat which can be liberated by combustion of a mole of the gas. Molar heating value is expressed in units of energy per mole. In the "lean mixture" embodiment, the molar flow rate of a gas, $n_g$, with units of moles per second, is multiplied by molar heating value. The result is the power of combustion described as $P_{gas}=H_m\, n_g$ and the change in combustion power between two selected power levels can be written as $\Delta P_{gas}=H_m\, \Delta n_g$. If the combustion power changes of the sample gas and reference gas are measured between the same two selected power levels (See FIG. 4a), then equating the two combustion power changes results in Eq. 1 as follows:

$$H_{ms} = H_{mr}\left(\frac{\Delta \dot{n}_r}{\Delta \dot{n}_s}\right) \quad (1)$$

where the subscripts r and s refer to the reference gas and the sample gas, respectively.

A desirable feature of this invention is that speed of response can be improved by terminating the individual measurement cycles prior to completion. If the changes in combustion power during the reference cycle and the sample cycle are not equal, but are related by a known ratio, then Eq. 1 can be modified introducing a correction factor, η, which is the ratio of the changes in combustion power and Eq. 1 can be restated as:

$$H_{ms} = \eta H_{mr}\left(\frac{\Delta n_R}{\Delta n_S}\right) \quad (2)$$

where η is the ratio of the two changes in combustion power. It should be clear that η can take on values that range between zero and unity.

A mole of gas contains a fixed number of molecules, known as Avogadro's number, and occupies a defined volume, Vm, which is a function of temperature and pressure. At 0° C. and 14.696 psia, the volume for an ideal gas is 22.4138 liters. The effect of compressibility must be recognized and used to define the molar volume of a real gas as $V_{m\ real} = V_{m\ ideal} Z_{real}$ with units of volume per mole and where the compressibility, $Z_{real}$, is calculated at the temperature and pressure of the measurement. Therefore the volume heating value (energy per unit volume) of the gas is stated as:

$$H_{vs} = \frac{\eta H_{mr}\left(\dfrac{\Delta \dot{n}_r}{\Delta \dot{n}_s}\right)}{V_{m\,ideal} Z_{real}} \quad (3)$$

The heating value, as defined in Eqs. (1) through (3), is related to a standard temperature and pressure according to the general gas laws and factors known in art of gas physics and gas measurement.

The molar flow rate of the gas flowing from volume chambers 5, 14 is sensed by measuring the rate of change or change of pressure in the volume as the gas is withdrawn. The relation between the molar flow rate of the gas and the rate of change of pressure is obtained from the general gas law and is expressed as follows:

$$\dot{n} = \frac{\dot{P}V}{Z^2 RT} \quad (4)$$

where n is the molar flow rate, P is the rate of change of pressure, and Z is the compressibility factor.

Figure 4B:
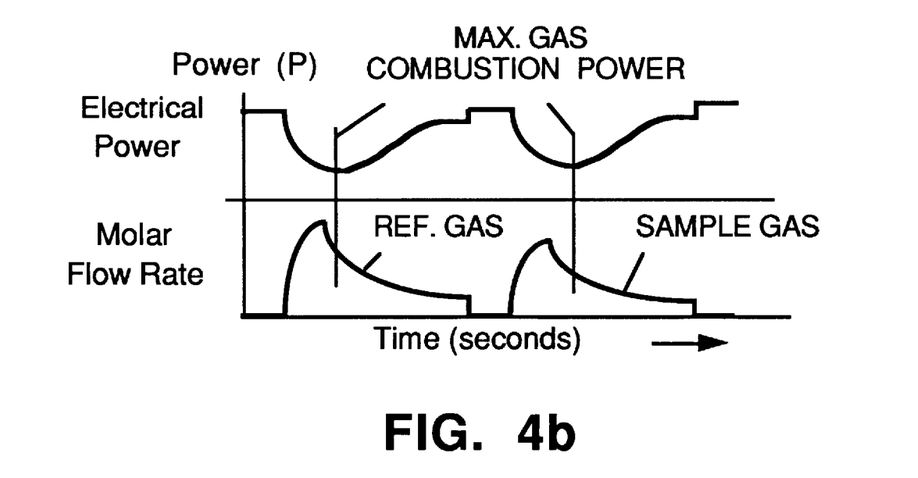

For the "rich mixture" embodiment, the reference gas is introduced at sufficiently frequent intervals to assure that humidity has not changed, and this allows ambient air to be used as the combustion supporting gas. If the reference gas is not introduced at such sufficiently frequent intervals, then the air is preferably dried to a very low humidity, such as less than 5% relative humidity. In the "rich mixture" embodiment, the maximum combustion temperature corresponding to the minimum power input level (See FIG. 4b) identifies the stoichiometric point of combustion. This embodiment requires the measurement of the molar flow rate of the gas, $n_g$ in units of moles per second. Since the stoichiometric points of the sample gas and reference gas are measured, the heating value is formed using a ratio of the molar flow rates (n) and the volume heating value (H) of the reference gas according to Eq. 5 as follows:

$$H_{vs} = H_{vr} \left( \frac{\dot{n}_r}{\dot{n}_s} \right) \qquad (5)$$

where the subscripts r and s refer to the reference gas and the sample gas, respectively.

FIGS. 4a and 4b illustrate the rate of combustion vs. molar flow rate for the "lean gas" mixture embodiment and the "rich mixture" embodiment, respectively.

When the gas flow is (valves 4 and 16 are closed), only air is supplied to the combustion material and the electrical power (P) supplied to the heated body of material is maximum and stable. If desired, a baseline signal can be detected for heater power when only air is passing through the combustion device 8. The temperature of the combustion material is constant, and this is represented by the constant levels of electrical power in FIGS. 4a and 4b. When reference gas or sample gas is flowed to the combustion heater, the combustion process adds heat to the body of material and the power controller reduces the electrical power (P) to the heater in the exact amount as gas energy is added. As the gas flow rate reduces due to reduced gas pressure in the volume chambers 5, 14, the combustion gas energy is reduced. The electrical power must then be increased to maintain a constant temperature in the heated material. When the temperature of combustion is at a maximum, the minimum electrical power needs to be supplied to heat the material, as shown in FIG. 4b.

As shown in FIG. 4a, molar flow rates for the reference gas are determined for two selected power levels. The molar flow rates for the sample gas are then determined for the same two selected power levels.

As shown in FIG. 4b, a rich gas mixture of the reference gas, containing more gas molecules than necessary for stoichiometric combustion, is flowed to the combustion material. As the reference gas flow rate reduces, the maximum combustion power state (minimum power level) is reached. There, the molar flow rate of the reference gas is measured. This cycle is then repeated for the sample gas, until the maximum combustion power state (minimum power level) is reached and the molar flow rate of the reference gas is measured. This data is read by the microcontroller 12, which then calculates heat content of the sample gas.

The flow rate of air through the porous material 26 is not critical and can vary by ±10% in a slow fashion, but must be stable between the reference and sample cycles. The methods of the invention are carried out at an ambient temperatures from approximately −40° F. to 130° F.

Figure 5:
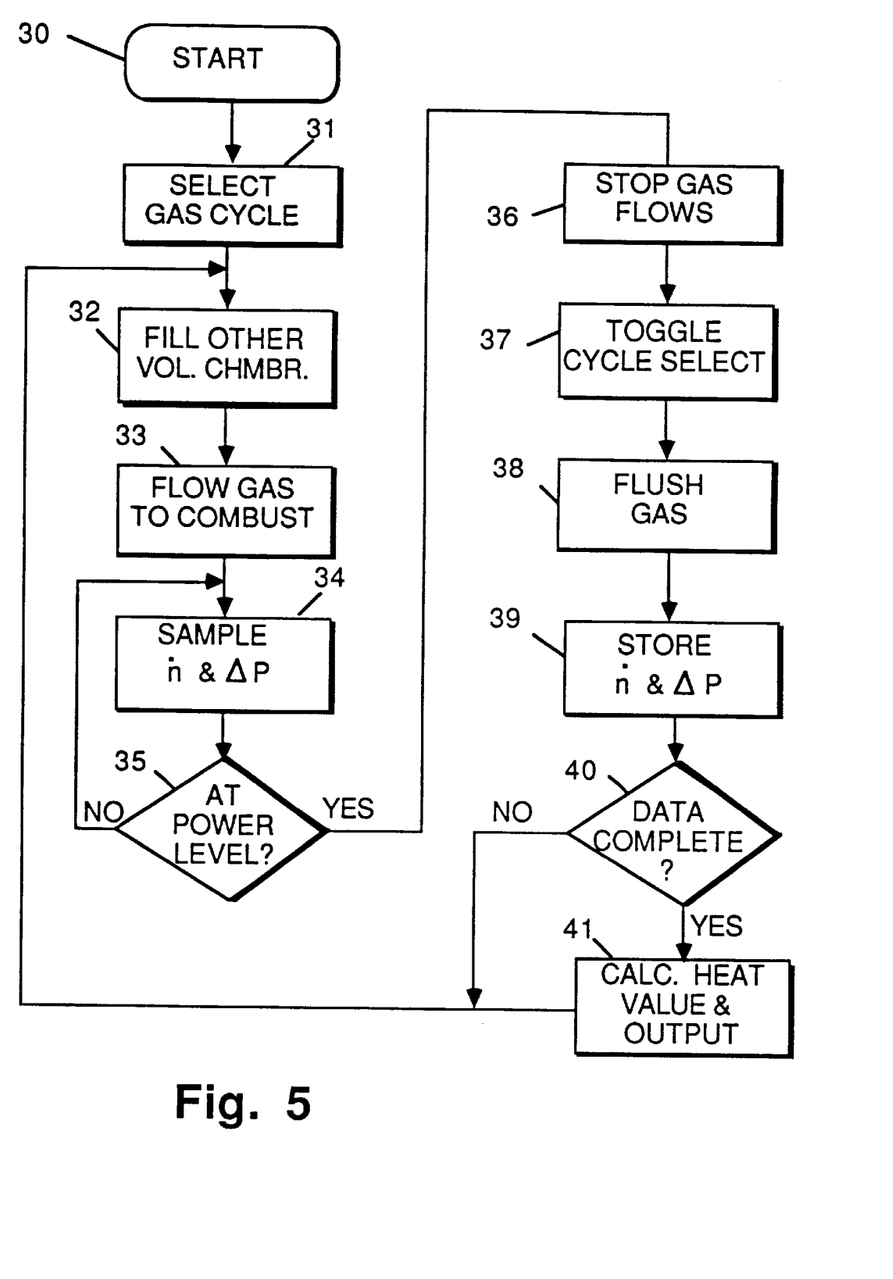
FIG. 5 is a flow chart of the operation of a microcontroller in the apparatus of FIG. 1.

FIG. 5 shows the operation from the viewpoint of the microcontroller 12 in executing its control program. The start of the operation is represented by start block 30. The microcontroller 12 executes instructions to select either the reference gas cycle or the sample gas cycle, as represented by process block 31. If the reference gas cycle is selected, the microcontroller 12 executes further instructions, represented by process block 32, to open valve 16 and allow sample gas to fill volume chamber 14 in preparation for the sample gas cycle. Next, as represented by process block 33, the microcontroller 12 executes further instructions to open valve 6 to allow reference gas to flow to the combustion device 8. The microcontroller 12 then executes instructions represented by process block 34 to begin to sample molar flow rate ($\dot{n}$) and the changes in the electrical power ($\Delta P$) required by the combustion device 8. The microcontroller 12 then executes instructions represented by decision block 35 to test for a molar flow rate corresponding to a maximum power of combustion (minimum electrical power) (FIG. 4b) or for molar flow rates corresponding to selected power levels (FIG. 4a). If the result is "NO," it loops back to continue with another sample. If the result is "YES," it proceeds to execute instructions represented by block 36 to end the first cycle and prepare for the next cycle.

As represented by process block 36, microcontroller 12 executes instructions to stop the gas flow of the reference gas by closing valve 6. The microcontroller 12 then executes instructions represented by process block 37 to change the selection to the other gas cycle. The microcontroller 12 then executes instructions represented by process block 38 to flush chamber 5 and combustion apparatus 8. Next, the microcontroller 12 then executes instructions represented by process block 39 to store the final flow rate and power values for the cycle just completed. A check is then made, as represented by decision block 40, to see if both a reference cycle and a sample gas cycle have been completed within a recent time period. If the result is "YES," the data can be used calculate heating value as represented by process block 41. The heating value is then output to a visual display (not shown in FIG. 1) or another type of output device. If the data is not complete, the result from decision block 40 is "NO," and program returns to start a new gas measurement cycle, such as the sample gas cycle, at block 32.

This has been a description of examples of how the invention can be carried out. Those of ordinary skill in the art will recognize that various details may be modified in arriving at other detailed embodiments, and these embodiments will come within the scope of the invention.

Therefore, to apprise the public of the scope of the invention and the embodiments covered by the invention, the following claims are made.

We claim:

1. An apparatus for determining the heating value of a sample gas, the apparatus comprising:

a heater structure of material containing at least one space with a linear dimension that is not greater than a quenching dimension for the sample gas so as to quench any flame produced by combustion of the sample gas;

a heater element disposed in the heater structure of material to heat a portion of the heater structure of material to a temperature sufficient for combustion of the sample gas;

a flow path for passing the sample gas into contact with the heater structure of material;

a sensor for sensing combustion of the sample gas and for generating a signal responsive thereto; and a processor responsive to signals from the sensor for computing the heating value of the sample gas.

2. The apparatus of claim 1, wherein said heater structure of material is formed of non-catalytic material.

3. The apparatus of claim 1, wherein said heater structure of material further comprises a plurality of solids arranged in a column with a plurality of spaces between said solids, so as provide a porous body of material.

4. The apparatus of claim 3, wherein said spaces have a linear dimension of not greater than about 2.5 mm.

5. The apparatus of claim 3, wherein said plurality of solids are beads of ceramic material.

6. The apparatus of claim 5, wherein said beads of ceramic material are graduated in size.

7. The apparatus of claim 6, wherein said ceramic material is a non-catalytic material.

8. The apparatus of claim 1, wherein said heater structure of material further comprises a casing and a body of ceramic material disposed in said casing;

wherein said heater element is disposed in said body of ceramic material; and wherein the heater structure of material has an interior space between said casing and said body of ceramic material with linear dimensions which are not greater than the quenching dimension for the sample gas.

9. The apparatus of claim 8, wherein said casing and said body of ceramic material are formed of non-catalytic material.

10. The apparatus of claim 8, wherein said heater element further comprises a coil of platinum wire contained in the body of ceramic material.

11. The apparatus of claim 8, wherein said interior space has linear dimensions of not greater than about 2.5 mm.

12. The apparatus of claim 8, wherein said casing has opposite ends with an entrance for the sample gas in one opposite end and an exit for the sample gas in another opposite end and wherein said apparatus further comprises filters disposed in said opposite ends of said casing.

13. A method for determining the heating value of a sample gas, the method comprising:

heating a structure of material to a temperature sufficient for combustion of the sample gas;

passing the sample gas into contact with the heated structure of material;

combusting the sample gas within the heated structure of material while quenching any flame produced by said combustion;

sensing a power of combustion released by combustion of the sample gas; and computing the heating value of the sample gas in response to the power of combustion released by combustion of the sample gas.

14. The method of claim 13, wherein heating the structure of material includes heating non-catalytic material within the structure of material.

15. The method of claim 13, wherein quenching any flame within the structure of material includes transferring heat from combustion of the sample gas to the structure of material at a rate sufficient for quenching any flame produced by said combustion.

16. The method of claim 13, further comprising the step of maintaining a sensor in the heated structure of material at approximately a constant temperature by adjusting the electrical power to a heater disposed in the heated structure of material.

17. The method of claim 13, further comprising the step of transmitting a signal representative of the heating value of the sample gas.

18. The method of claim 13, further comprising the step of limiting the supply of sample gas to supply less combustion energy than an amount of electrical energy supplied to heat the structure of material.

19. The method of claim 13, wherein sensing a power of combustion released by combustion of the sample gas includes sensing a signal from a sensor in the heated structure of material, and wherein said signal represents a reduction in electrical power required to maintain an approximately constant temperature of the sensor in the heated structure of material.

20. The method of claim 13, wherein said method is performed at ambient temperatures from approximately −40° F. to 130° F.

21. The method of claim 13, wherein the step of sensing a power of combustion released by combustion of the sample gas includes sensing a temperature of the heated structure of material through a constant resistance bridge circuit.

* * * * *

UNITED STATES PATENT AND TRADEMARK OFFICE
CERTIFICATE OF CORRECTION

PATENT NO. : 5,882,115                     Page 1 of 2

DATED : March 16, 1999

INVENTOR(S) : Vander Heyden et al.

It is certified that error appears in the above-identified patent and that said Letters Patent is hereby corrected as shown below:

Column 1, line 6, "516,705" should be --5,816,705--.

Column 2, line 19, "combusting" should be --combustion--.

Column 2, line 55 "f low" should be --flow--.

Column 2, line 66, "f low" should be --flow--.

Column 7, line 58, "combusting" should be --combustion--.

Column 8, line 3, "$n_g$" should be --$\dot{n}_g$--.

Column 8, line 5, "$n_g$" should be --$\dot{n}_g$--.

Column 8, line 7, "$\Delta n_g$" should be --$\Delta \dot{n}_g$--.

Column 8, equation (1), "$H_{ms}$" should be --$H_{m\,s}$--.

Column 8, equation (1), "$H_{mr}$" should be --$H_{m\,r}$--.

UNITED STATES PATENT AND TRADEMARK OFFICE
CERTIFICATE OF CORRECTION

PATENT NO. : 5,882,115
DATED : March 16, 1999
INVENTOR(S) : Vander Heyden, et al It is certified that error appears in the above-identified patent and that said Letters Patent is hereby corrected as shown below:

Column 8, equation (2), "$H_{ms}$" should be --$H_m$ $_s$--.

Column 8, equation (2), "$H_{mr}$" should be --$H_m$ $_r$--.

Column 9, equation (5), "$H_{vs} = H_{vr}$" should be --$H_v$ $_s$ = $H_v$ $_r$--.

Column 9, line 7, "$n_g$" should be --$\dot{n}_g$--.

Column 9, line 10, "(n)" should be --$(\dot{n})$--.

Column 9, line 20, "flow is" should be --flow is not present--.

Column 9, line 47, "state" should be deleted.

Column 9, line 50, "state" should be deleted.

Signed and Sealed this

Fourteenth Day of September, 1999

Attest:

Attesting Officer

Q. TODD DICKINSON

Acting Commissioner of Patents and Trademarks